United States Patent
Miyamoto et al.

(10) Patent No.: US 7,314,740 B2
(45) Date of Patent: Jan. 1, 2008

(54) METHOD OF SEPARATING POLY-3-HYDROXYALKANOIC ACID

(75) Inventors: Kenji Miyamoto, Yokohama (JP); Noriko Ogawa, Kobe (JP); Fumio Osakada, Okayama (JP); Keiji Matsumoto, Nishinomiya (JP)

(73) Assignee: Kaneka Corporation, Osaka (JP)

( * ) Notice: Subject to any disclaimer, the term of this patent is extended or adjusted under 35 U.S.C. 154(b) by 306 days.

(21) Appl. No.: 10/507,414

(22) PCT Filed: Apr. 25, 2003

(86) PCT No.: PCT/JP03/05323

§ 371 (c)(1),
(2), (4) Date: Apr. 7, 2005

(87) PCT Pub. No.: WO03/091444

PCT Pub. Date: Nov. 6, 2003

(65) Prior Publication Data

US 2006/0099695 A1  May 11, 2006

(30) Foreign Application Priority Data

Apr. 26, 2002   (JP) .............................. 2002-125881

(51) Int. Cl.
*C12P 7/62* (2006.01)
(52) U.S. Cl. .................................... 435/135
(58) Field of Classification Search ................. 435/135
See application file for complete search history.

(56) References Cited

U.S. PATENT DOCUMENTS

| | | |
|---|---|---|
| 4,358,583 A | 11/1982 | Walker et al. |
| 5,952,460 A | 9/1999 | Liddell et al. |
| 7,083,972 B2 * | 8/2006 | Yokomizo et al. ...... 435/254.2 |

2004/0014197 A1 *   1/2004   Huisman et al. .......... 435/252.3

FOREIGN PATENT DOCUMENTS

| | | |
|---|---|---|
| JP | 55 118394 | 9/1980 |
| JP | 57 65193 | 4/1982 |
| JP | 63 198991 | 8/1988 |
| JP | 2 69187 | 3/1990 |
| JP | 4 61638 | 10/1992 |
| JP | 7 31487 | 2/1995 |
| JP | 7 31488 | 2/1995 |
| JP | 7 31489 | 2/1995 |
| JP | 7 79788 | 3/1995 |
| JP | 7 177894 | 7/1995 |
| JP | 8 502415 | 3/1996 |
| JP | 11 266891 | 10/1999 |
| JP | 2001 46094 | 2/2001 |
| WO | WO 94/10289 | 5/1994 |

OTHER PUBLICATIONS

Choi, Jong-il, et al., "Efficient and Economical Recovery of Poly(3-Hydroxybutyrate) from Recombinant *Escherichia coli* by Simple Digestion with Chemicals", *Biotechnology and Bioengineering*, vol. 62, No. 5, Mar. 5, 1999, pp. 546-553.

Doi, Yoshiharu, et al., "Microbial Synthesis and Characterization of Poly(3-hydroxybutyrate-*co*-3-hydroxyhexanoate)", *MACROMOLECULES*, vol. 28, No. 14, Jul. 3, 1995, pp. 4822-4828.

Harrison, Susan T.L., et al., "Combined chemical and mechanical processes for the disruption of bacteria", *BIOSEPARATION*, vol. 2, No. 2, 1991, pp. 95-105.

* cited by examiner

*Primary Examiner*—Herbert J. Lilling
(74) *Attorney, Agent, or Firm*—Kenyon & Kenyon LLP

(57) ABSTRACT

The invention aims at providing a method of producing a poly-3-hydroxyalkanoic acid, which comprises carrying out a physical disruption treatment of a suspension of poly-3-hydroxyalkanoic acid-containing microbial cells with adding an alkali thereto either continuously or intermittently and, thereafter, separating the poly-3-hydroxyalkanoic acid.

9 Claims, 1 Drawing Sheet

(a)

(b)

METHOD OF SEPARATING POLY-3-HYDROXYALKANOIC ACID

This application is a 371 national phase application of PCT/JP03/05323 filed on 25 Apr. 2002, claiming priority to JP 2002-125881, filed on 26 Apr. 2002, the contents of which are incorporated herein by reference in their entirety.

TECHNICAL FIELD

The present invention relates to a method for the separation and purification of poly-3-hydroxyalkanoic acids from microbial cells.

BACKGROUND ART

Poly-3-hydroxyalkanoic acids (hereinafter sometimes referred to collectively as PHA) are the thermoplastic polyesters which are elaborated and accumulated as energy storage substances by a variety of microorganisms and have biodegradability. In these days waste plastics are disposed of by incineration or burial but these methods of disposal are causative of global warming and ground loosening of reclaimed lands, among other disadvantages. Therefore, with the growing public awareness of the importance of plastics recycling, ways and means for systematized recycling are being explored. However, uses amenable to such recycling are limited and actually the disposal load of waste plastics cannot be completely liquidated by said incineration, burial, and recycling but rather a large proportion of the disposal load is not disposed of but simply left exposed to the elements. There is accordingly a mounting interest in PHA and other biodegradable plastics which, after disposal, would be incorporated into the natural cycle of matter and degradation products of which would not exert ecologically deleterious influences, and their practical utilization are highly desired. Particularly the PHA which microorganisms elaborate and accumulate in their cells is taken up in the carbon cycle of the natural kingdom and it is, therefore, predicted that it will not have any appreciable adverse effects on the ecosystem. In the field of medical treatment, too, it is considered possible to use PHA as an implant material which does not require recovery or a vehicle for drug delivery.

Since the PHA elaborated by microorganisms usually form granules and is accumulated intracellularly, exploitation of PHA as a plastic requires a procedure for separating it from microbial cells. The known technology for the separation and purification of PHA from microbial cells can be roughly classified into the technology which comprises extracting PHA from the cells with an organic solvent in which PHA is soluble and the technology which comprises removing the cell components other than PHA by cell disruption or solubilization.

Referring to the separation and purification technology of PHA involving extraction with an organic solvent, the extraction technique utilizing a halogen-containing hydrocarbon, such as 1,2-dichloroethane or chloroform, as the solvent in which PHA is,soluble is known (Japanese Kokai Publication Sho-55-118394, Japanese Kokai Publication Sho-57-65193). However, since these halogen-containing hydrocarbons are hydrophobic solvents, a pre-extraction procedure, such as drying the cells in advance or otherwise, allowing the solvent to directly contact the intracellular PHA is required. Moreover, in such a technology, dissolving PHA at a practically useful concentration (for example, 5%) or higher gives only an extract which is so highly viscous that it involves considerable difficulties in separating the undissolved residues of microbial cells from the PHA-containing solvent layer. Furthermore, in order that PHA may be reprecipitated from the solvent layer at a high recovery, some PHA-insoluble solvent, such as methanol or hexane, need to be used in a large quantity, e.g. 4 to 5 volumes based on the solvent layer, and thus a vessel of large capacity is required for reprecipitation. In addition, the necessary quantity of solvents is so large that both the solvent recovery cost and the cost of lost solvents are enormous. Furthermore since the use of organohalogen compounds tends to be limited these days for protection of the environment, industrial application of this technology has many obstacles to surmount.

Under the circumstances, there has been proposed an extraction technology using a solvent which is not only capable of dissolving PHA but also miscible with water, for example a hydrophilic solvent such as dioxane (Japanese Kokai Publication Sho-63-198991), propanediol (Japanese Kokai Publication Hei-02-69187), or tetrahydrofuran (Japanese Kokai Publication Hei-07-79788). These methods appear to be favorable partly because PHA can be extracted not only from dry cells but also from wet cells and partly because precipitates of PHA can be obtained by mere cooling of the solvent layer separated from the microbial cell residues. However, even with these methods, the problem of high viscosity of the PHA-containing solvent layer remains to be solved. In addition, while heating is required for enhancing the extraction efficiency, the heating in the presence of water unavoidably results in a decrease in molecular weight due to hydrolysis of PHA and a poor recovery of PHA.

On the other hand, as the technology of removing the cell components other than PHA by solubilization for separation of PHA, J. Gen. Microbiology, 19, 198-209 (1958) describes a technology which comprises treating a suspension of microbial cells with sodium hypochlorite to solubilize cell components other than PHA and recovering PHA. This technology is simple process-wise but the necessity to use a large amount of sodium hypochlorite is a factor leading to a high production cost. Moreover, in view of the marked decrease in molecular weight of PHA and the appreciable amount of chlorine left behind in PHA, this technology is not considered to be suitable for practical use. Japanese Kokoku Publication Hei-04-61638 describes a process for separating PHA which comprises subjecting a suspension of PHA-containing microbial cells to a heat treatment at a temperature of 100° C. or higher to disrupt the cellular architecture and, then, subjecting the disrupted cells to a combination treatment with a protease and either a phospholipase or hydrogen peroxide to solubilize the cell components other than PHA. This technology is disadvantageous in that because the heat treatment induces denaturation and insolubilization of the protein, the load of subsequent protease treatment is increased and that the process involves many steps and is complicated.

As a technology for disrupting PHA-containing microbial cells, there also has been proposed a method which comprises treating microbial cells with a surfactant, decomposing the nucleic acids released from the cells with hydrogen peroxide, and separating PHA (Japanese Kohyo Publication Hei-08-502415) but the waste liquor containing the surfactant develops a copious foam and, in addition, has a high BOD load value. From these points of view, the use of a surfactant is objectionable for production on a commercial scale.

There has also been proposed a technology for separating PHA which comprises disrupting PHA-containing microbial cells with a high-pressure homogenizer (Japanese Kokai Publication Hei-07-177894 and Japanese Kokai Publication Hei-07-31488). However, this technology has the drawback that although a suspension of microbial cells is subjected to a high-pressure treatment at least 3 times, or 10 times at elevated temperature depending on cases, the purity of PHA that can be attained is as low as about 65 to 89%. There has also been proposed a technology for separating PHA which comprises adding an alkali to a suspension of PHA-containing microbial cells, heating the suspension, and disrupting the cells (Japanese Kokai Publication Hei-07-31487). However, this technology is disadvantageous in that the purity of the product polymer that can be attained is as low as 75.1 to 80.5% and that if the level of addition of the alkali be raised to improve the yield, the molecular weight of the polymer would be decreased. Several techniques for carrying out physical disruption after addition of an alkali have been proposed (Bioseparation, 2, 95-105, 1991, Japanese Kokai Publication Hei-07-31489) but since the alkali treatment alone results in the extracellular release of only a small amount of cell components and some of such cell components are retained in the PHA fraction even after subsequent high-pressure disruption treatment, these techniques are invariably inefficient. Thus, PHA of high purity cannot be separated unless the microbial cell suspension is subjected to at least 5 cycles of high-pressure treatment and even then the purity of PHA is as low as about 77 to 85%. The technologoy involving addition of an alkali has an additional drawback; generally the cell components released from microbial cells, particularly nucleic acids, increase the viscosity of the cell suspension to make subsequent processing difficult.

There has also been proposed a technology in which a suspension of PHA-containing microbial cells is adjusted to an acidity lower than pH 2 and PHA is separated at a temperature not below 50° C. (Japanese Kokai Publication Hei-11-266891). However, this technology is disadvantageous in that the treatment under the strongly acidic condition below pH 2 is undesirable for production on a commercial scale, that the acid treatment must be followed by adjustment to the alkaline side for enhanced purity but this entails massive salt formation, and that the molecular weight of the product PHA is decreased from 2,470,000 to about 1,000,000.

SUMMARY OF THE INVENTION

The object of the present invention is to overcome the above disadvantages of the prior art and accordingly provide a technology of separating and purifying PHA which is capable of removing the cell components other than PHA with good efficiency from PHA-containing microbial cells and giving PHA of high purity in high yields in only a few steps without incurring any serious decrease in molecular weight of PHA.

The inventors of the present invention explored in earnest for a commercially useful PHA production technology. As a result they found (i) that when a physical disruption treatment of a suspension of PHA-containing microbial cells is carried out with adding an alkali thereto either continuously or intermittently, the viscosity elevation of the suspension due to the release of cell components other than PHA from the cells can be prevented, (ii) that pH control of the suspension is rendered feasible by the above prevention of viscosity elevation of the suspension, and (iii) that by this feasiblity of suspension pH control, the treatment at a low alkali concentration can be made possible with the consequent advantage that PHA of high purity can be separated without incurring a marked decrease in molecular weight. The present invention has been developed on the basis of the above findings.

The present invention, therefore, relates to a method of producing a poly-3-hydroxyalkanoic acid, which comprises carrying out a physical disruption treatment of a suspension of poly-3-hydroxyalkanoic acid-containing microbial cells with adding an alkali thereto and, thereafter, separating the poly-3-hydroxyalkanoic acid.

In one preferred mode of practicing the invention, the present invention relates to the method, wherein said addition of an alkali is carried out with controlling the pH of the suspension, more preferably the PH of the suspension between 9 and 13.5. It should also be understood that said physical disruption treatment of the suspension is preferably carried out under stirring of said suspension. Furthermore, said physical disruption treatment of the suspension is preferably carried out at the temperature not less than 20° C. and below 40° C.

In another preferred mode of practicing the invention, the present invention relates to the method, wherein the poly-3-hydroxyalkanoic acid is a copolymer comprising of D-3-hydroxyhexanoate (3HH) and one or more other 3-hydroxyalkanoic acids. More preferably, the present invention relates to the method, wherein the poly-3-hydroxyalkanoic acid is a binary copolymer comprising of D-3-hydroxybutyrate (3HB) and D-3-hydroxyhexanoate (3HH) or a ternary copolymer comprising of D-3-hydroxybutyrate (3HB), D-3-hydroxyvalerate (3HV), and D-3-hydroxyhexanoate (3HH).

In a still another preferred mode, the present invention relates to the method, wherein the poly-3-hydroxyalkanoic acid-containing microbial cells are cells of *Aeromonas caviae* or cells of a strain of microorganism transformed by a poly-3-hydroxyalkanoic acid synthase group gene derived from *Aeromonas caviae*.

The present invention is now described in detail.

DETAILED DESCRIPTION OF THE INVENTION

The microorganism for use in the present invention is not particularly restricted provided that it is a microorganism containing PHA as intracellularly accumulated. For example, microorganisms of the genus *Alcaligenes*, such as *A. lipolytica*, *A. eutrophus*, *A. latus*, etc.; those of the genus *Pseudomonas*; those of the genus *Bacillus*, those of the genus *Azotobacter*; those of the genus *Nocardia*; and those of the genus *Aeromonas* can be mentioned. Particularly preferred are strains of *Alcaligenes caviae*, and further are strains of *Alcaligenes eutrophus* AC32 transformed by a PHA synthase group gene derived therefrom (deposited on Budapest Treaty, international depositary authority: National Institute of Advanced Industrial Science and Technology International Patent Organism Depositary, 1-3 Higashi 1 chome, Tsukuba-shi, Ibaraki-ken, Japan, date of transfer: Aug. 7, 1997, Accession No. FERM BP-6038, as transferred from FERM P-15786 originally deposited Aug. 12, 1996 (J. Bacteriol., 179, 4821-4830 (1997)). In the present invention, such a strain of microorganism is cultured under suitable conditions to let it accumulate PHA intracellularly and its cells are used. The cultural method is not particularly restricted but the known method described in Japanese Kokai Publication Hei-05-93049, among others, can for example be employed.

The term "PHA" as used in this specification is a generic term meaning any and all polymers of hydroxyalkanoic acids. Although the hydroxyalkanoic acid units of such polymers are not particularly restricted, a homopolymer comprising of D-3-hydroxybutyrate (3HB), a copolymer of 3HB and one or more other 3-hydroxyalkanoic acids, and a copolymer of various 3-hydroxyalkanoic acids inclusive of D-3-hydroxyhexanoate (3HH) can be mentioned by way of example. Particularly preferred from the standpoint of physical characteristics of the product polyester is the polymer containing 3HH as a monomeric unit, for example a binary copolymer comprising of 3HB and 3HH (Macromolecules, 28, 4822-4828 (1995)) or a ternary copolymer comprising of 3HB, D-3-hydroxyvalerate (3HV), and 3HH (Japanese Patent No. 277757, Japanese Kokai Publication Hei-08-289797). The compositional ratio of the monomer units constituting a binary copolymer comprising of 3HB and 3HH is not particularly restricted but copolymers containing 1 to 99 mol % of the 3HH unit are suitable. The compositional ratio of the monomer units constituting a ternary copolymer comprising of 3HB, 3HV, and 3HH is not particularly restricted, either, but copolymers containing 1 to 95 mol % of the 3HB unit, 1 to 96 mol % of the 3HV unit, and 1 to 30 mol % of the 3HH unit are preferred.

The PHA content of the microbial cells to be treated is preferably as high as possible, of course. In the treatment on a commercial scale, the PHA content of dry cells is preferably not less than 20 weight %, and when the alkali treatment, physical disruption treatment, separation procedure, and purity of the separated polymer, among other factors, are taken into consideration, the particularly preferred PHA content is not less than 50 weight %.

The term "a suspension of microbial cells" as used in this specification means a culture medium available on completion of culture as is or an aqueous suspension of the cells harvested from a culture medium by centrifugation or the like technique. The concentration of cells in the suspension on a dry cell basis is preferably not more than 500 g/L, more preferably not more than 300 g/L.

The alkali for use in the practice of the invention is not particularly restricted provided that the suspension pH may be controlled within the herein-defined range, and includes alkali metal hydroxides such as sodium hydroxide, potassium hydroxide, lithium hydroxide, etc.; alkali metal carbonates such as sodium carbonate, potassium carbonate, etc.; alkali metal hydrogen carbonates such as sodium hydrogen carbonate, potassium hydrogen carbonate, etc.; organic acid alkali metal salts such as sodium acetate, potassium acetate, etc.; alkali metal borates such as borax etc.; alkali metal phosphates such as trisodium phosphate, disodium hydrogen phosphate, tripotassium phosphate, dipotassium hydrogen phosphate, etc., and aqueous ammonia, among others. Among these, sodium hydroxide, sodium carbonate, and potassium hydroxide are preferred in terms of suitability for commercial production and in cost terms. The alkali may be added directly but is preferably added in the form of an aqueous solution.

The physical disruption treatment in the present invention includes not only sonication but also disruption with an emulsification-dispersion machine, a high-pressure homogenizer, a mill or the like. The high-pressure homogenizer referred to above is not particularly restricted but may include Manton-Gaulin manufactured by APV Gaulin, Germany, Mini-Lab manufactured by APV Rannie, Demmark, and Microfluidizer manufactured by Microfluidics, USA, among others. The mill referred to above is not particularly restricted but includes DYNO-Mill manufactured by Willy A. Bachofen, Switzerland, to mention an example. The emulsification-dispersion machine referred to above is not particularly restricted, either, but includes SILVERSON MIXER manufactured by Silverson Machines, Inc., England, Clearmix manufactured by M-TECHNIQUE, Japan, and Ebara Milder manufactured by Ebara Corporation, Japan, among others. These machines are not exclusive choices but any machine capable of causing efficient disruption of nucleic acids, which are released from cells in the alkali treatment and otherwise mainly play a part in causing suspension viscosity elevation, and, at the same time, capable of effecting sufficient dispersion of insoluble substance other than the objective polymer, such as the cell wall, cell membrane, and insoluble protein, can be employed. Furthermore, the purity of the polymer can be enhanced by operating two or more of the above-mentioned kinds of disrupting machines concurrently or in succession.

The physical disruption treatment referred to above can be carried out under stirring of said suspension. Stirring means which can be used is not particularly restricted but may be any means capable of producing the ordinary mechanical stirring effect.

In the present invention, the physical disruption treatment of a suspension of PHA-containing microbial cells is carried out with adding the alkali either continuously or intermittently. By this alkali treatment, insoluble substances such as nucleic acids, cell wall, cell membrane and insoluble protein are released along with PHA from the microbial cells. As the physical disruption treatment is carried out simultaneously, the cells are completely disrupted and the released constituents are micronized to prevent viscosity elevation and promote the alkali solubilization of insoluble substances, thus contributing to enhanced PHA yields.

In the present invention, said physical disruption treatment and alkali addition may be carried out concurrently or the physical disruption treatment may be started in advance of the start of alkali addition. As a further alternative, said physical disruption treatment and alkali addition may be carried out in an alternating fashion, or following said physical disruption treatment and alkali addition, the physical disruption treatment alone may be further continued.

In the present invention, it is preferable to control the pH of said suspension at the time of alkali addition. The control target pH value is preferably not less than pH 9, more preferably not less than pH 10. Moreover, the pH is controlled still more preferably at not more than pH 13.5, further more preferably not more than pH 13. If the pH exceeds 13.5, marked decomposition of PHA may take place. If the pH is less than 9, the PHA separation effect tends to be sacrificed in some cases. The latitude of pH control is preferably within ±1 of the set value, more preferably within ±0.5 of the set value.

In the practice of the invention, the addition of the alkali is preferably carried out either continuously or intermittently with controlling the pH of said suspension.

The inventors of the present invention found empirically that, in the separation and purification of PHA from microbial cells, the addition of the whole amount of alkali at one time as in the prior art results in the exposure of PHA to a high concentration of alkali immediately after addition to cause a decrease in molecular weight of PHA and lead to a progressive depression of pH resulting from the consumption of the alkali as the reaction proceeds so that the efficient extraction cannot be consistently carried through. Moreover, in the technology involving addition of a predetermined amount of alkali to microbial cells, the culture medium components contained in the cell suspension, if they are acidic substances, react with the alkali or give rise to a buffered condition, thus failing to achieve the expected result. In contrast, according to the preferred technology of the invention, in which the addition of the alkali is carried out either continuously or intermittently to control the pH on the alkaline side, the insoluble substance can be effectively dissolved to realize an effective separation of PHA. Moreover, since the level of addition of the alkali is controlled not according to the absolute amount of alkali to be added but according to the pH, reproducible results can be obtained without being affected by the cultural conditions used, the time following culture till cell disruption, or the secondary substances occurring in the cell suspension.

From the standpoint of pH control, too, it is necessary that the physical disruption treatment of the suspension should be carried out with adding an alkali to the suspension. If the addition of an alkali is not carried out in the physical disruption treatment, the viscosity of the cell suspension is increased as mentioned above to interfere with stirring so that the pH cannot be controlled. As a consequence, a concentration distribution of the alkali added takes place with the consequent local elevation of alkali concentration inducing a decrease in molecular weight of PHA.

In the present invention, unlike in the prior art, physical disruption treatment and alkali addition need not be carried out at high temperature for separating PHA from PHA-containing microbial cells. Rather, a high-temperature treatment under alkaline conditions should be avoided, for otherwise it would induce a decrease in molecular weight of PHA. The preferred temperature for physical disruption treatment and alkali addition in the present invention is not over 50° C., more preferably not over 40° C., still more preferably below 40° C. The lower limit is preferably 20° C., more preferably 25° C.

FIGS. 1(a) and (b) are schematic diagrams showing exemplary equipment for microbial cell disruption for use in the separation and purification of PHA according to the invention. Of course, the mode of carrying out the invention is by no means limited to the one using the illustrated equipment.

The reference numeral 1 generally indicates the microbial cell disrupting equipment according to the invention. The reference numeral 6, in FIGS. 1(a) and (b), indicates a pH control agent strage tank adapted to hold a reserve of the alkali, and the pH control agent in this pH control agent strage tank 6 is fed by a pump 4 to a cell disruption tank 11 through a pipeline 5 to adjust the pH of a microbial suspension in the cell disruption tank 11. This cell disruption tank 11 is equipped with a stirring means 2 for uniformly stirring and mixing the pH control agent from the pH control agent strage tank 6 with the microbial cell suspension in the cell disruption tank 11. The same cell disruption tank 11 is further equipped with a pH detection-control means consisting of a pH meter 7 and a pH sensor-controller for detecting the pH of the microbial cell suspension in the cell disruption tank 11 and controlling the rate of feed of the pH control agent by said pump 4 so that a predetermined pH level may be established.

Referring to FIG. 1(a), the microbial cell suspension in the cell disruption tank 11 is fed by a pump 10 to a disrupting device 9 which is adapted to efficiently disrupt the nucleic acids otherwise causative of viscosity elevation as released from the microbial cells and feed the cells to the cell disruption tank 11 via a pipeline 8. In this arrangement, the viscosity of the cell suspension in the cell disruption tank 11 is held low and the cell suspension is homogenized by the stirring means 2, thus making it possible to strictly control the pH of the cell suspension.

Referring to FIG. 1(b), a disrupting device 12 is equipped within the cell disruption tank 11 so that the nucleic acids otherwise causative of viscosity elevation as released from the microbial cells may be efficiently disrupted by said disrupting device 12 within said cell disruption tank 11. Moreover, in the case where the disrupting device 12 has both the function to disrupt the nucleic acids and the function to uniformly stir the cell suspension, the stirring means 2 illustrated in the diagram (b) may be omitted.

PHA as obtained by the method of the invention is of high purity but depending on the intended use, the purity of this polymer may be further improved by the known purification technology using, for example, a lytic enzyme such as lysozyme (Japanese Kokoku Publication Hei-04-61638), a protease such as trypsin or pronase (Japanese Kokai Publication Hei-05-336982), or a peroxide such as hydrogen peroxide (Japanese Kohyo Publication Hei-08-502415).

BEST MODE FOR CARRYING OUT THE INVENTION

The strain of microorganism used in this example is *Alcaligenes eutrophus* AC32 (detailed information for accession are given hereinabove) transformed by a PHA synthase group gene derived from *Aeromonas caviae*. This strain was cultured in accordance with the protocol given in J. Bacteriol., 179, 4821-4830 (1997) to harvest bacterial cells containing about 60 wt % of poly(D-3-hydroxybutyrate-co-D-3-hydroxyhexanoate) [hereinafter sometimes referred to briefly as p(3HB-co-3HH)] having an average molecular weight of 1,000,000. The culture medium thus obtained was centrifuged (5,000 rpm, 10 min) to separate the cells and this pasty cellular fraction was diluted with water to prepare an aqueous suspension of 50 g cells/L concentration. This aqueous suspension was subjected to the following Examples, although the invention is by no means limited to the particular Examples.

The purity of the p(3HB-co-3HH) separated from the cells has determined as follows. A precipitate, 10 mg, as separated from the cells was dissolved in 1 ml of chloroform and treated with 0.85 ml of methanol and 0.25 ml of concentrated sulfuric acid at 100° C. for 140 minutes. After cooling, 0.5 ml of a saturated aqueous solution of ammonium sulfate was added and the mixture was stirred vigorously and, then, allowed to stand. The bottom layer was analyzed by capillary gas chromatography to determine the purity of the separated p(3HB-co-3HH).

The molecular weight of the p(3HB-co-3HH) separated from the bacterial cells was determined as follows. The precipitate (10 mg) separated from the bacterial cells was dissolved in 1 ml of chloroform and the solution was filtered to remove the insoluble substance. The filtrate was analyzed with SHIMADZU Corporation's GPC System fitted with Tosoh Corporation's TSK-GEL GMHXL (7.8×300 mm, two columns connected in series) using chloroform as the mobile phase.

EXAMPLE 1

Figure 1:
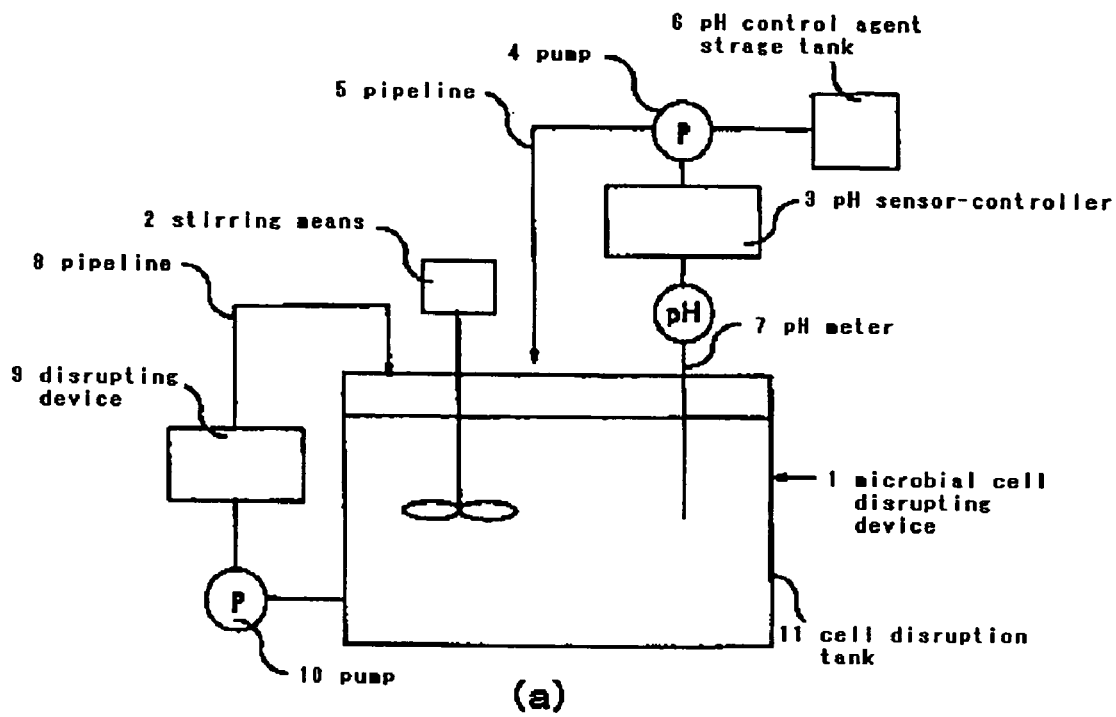
FIGS. 1(a) and (b) are schematic diagrams showing examples of the equipment for disrupting microbial cells in practicing the method of producing PHA according to the invention.
Figure 1:
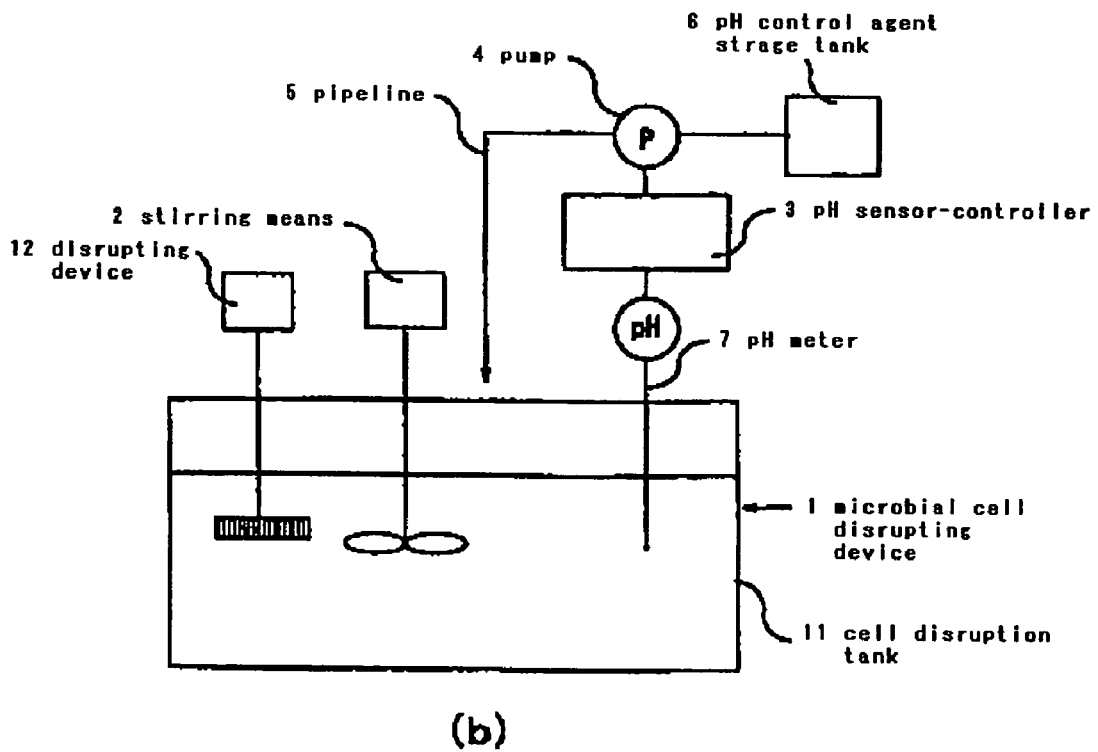

Using the p(3HB-co-3HH)-containing bacterial cells, 500 mL of a cell suspension was prepared and this suspension was placed in a 1 L reaction vessel equipped with a pH electrode and SILVERSON MIXER and incubated at 35° C. The pH electrode was connected to Lab Controller MDL-6C manufactured by B. E. Marubishi Co., Ltd. and the operation parameters were so set that when the pH of the suspension had dropped below a set value, a peristaltic pump would be actuated to deliver an aqueous solution of sodium hydroxide into the suspension until a set value had been reached. This operation protocol corresponds to the cell disruption equipment illustrated in FIG. 1(b). With the rotational speed of the SILVERSON MIXER set to 3,000 rpm and the pH setting of Lab Controller aligned to 11.8, stirring was continued for 2 hours (40 ml of 1 N aqueous solution of sodium hydroxide was required during this time). The treated suspension was centrifuged (3,000 rpm, 10 min) to give a precipitate. The precipitate was washed once with water and twice with methanol and dried under reduced pressure to recover a powder of p(3HB-co-3HH). The purity of this p(3HB-co-3HH) powder was as high as 92% and the average molecular weight of the product polymer was 870,000.

EXAMPLE 2

Except that the pH of the suspension was adjusted with an aqueous solution of sodium carbonate and the pH was set to 11.0, the procedure of Example 1 was otherwise repeated. The purity of the p(3HB-co-3HH) powder thus obtained was as high as 91% and the average molecular weight of the polymer was 890,000.

EXAMPLE 3

The Lab Controller described above was set to pH 11.8 as in Example 1 and stirring was carried out for 1 hour. The treated suspension was fed to Manton-Gaulin manufactured by APV Gaulin, Germany, and a physical disruption treatment was further carried out at 7,000 psi. After this treatment, the suspension was centrifuged (3,000 rpm, 10 min) to give a precipitate. This precipitate was washed once with water and twice with methanol and dried under reduced pressure to give a powder of p(3HB-co-3HH). This p(3HB-co-3HH) powder was exceptionally pure, i.e. 99%, and the average molecular weight of the polymer was 870,000.

COMPARATIVE EXAMPLE 1

Except that a mechanical stirrer (100 rpm) was used in lieu of SILVERSON MIXER for stirring, the procedure of Example 1 was otherwise repeated. The mechanical stirrer mentioned above is merely capable of stirring the suspension and not capable of physical disruption, with the result that addition of an alkali resulted in a viscosity elevation of the suspension to interfere with stirring and, thus, prevented accurate pH measurement. The suspension was centrifuged (15,000 rpm, 10 min) but no precipitate could be obtained.

COMPARATIVE EXAMPLE 2

Except that the pH control using Lab Controller was not carried out and 1 N aqueous solution of sodium hydroxide (40 ml) was added all at once, followed by 2 hours of stirring with SILVERSON MIXER, the procedure of Example 1 was otherwise repeated. As a result, the purity of the p(3HB-co-3HH) powder obtained was as high as 90% but the average molecular weight of the polymer was 300,000, indicating a marked decrease in molecular weight.

COMPARATIVE EXAMPLE 3

An alkali treatment was carried out under the conditions described in the best mode section of Japanese Kokai Publication Hei-07-31487. Thus, using the p(3HB-co-3HH)-containing bacterial cells, 500 ml of a cell suspension of 40 g/L concentration was prepared. Then, the pH of the suspension was adjusted to either 4 mM or 8 mM with 0.1 M aqueous solution of sodium hydroxide, and the suspension was stirred at 80° C. for 1 hour with heating. Each treated suspension was cooled to room temperature and centrifuged for separating a precipitate but no precipitate was obtained at the same rotational speed of 2700 rpm as used in the best mode section. Therefore, the suspension was diluted with equal volume of methanol and centrifuged at 8,000 rpm for 30 minutes to prepare a precipitate. This precipitate was washed once with water and twice with methanol and dried under reduced pressure to give a powder of p(3HB-co-3HH). In each case of 4 mM or 8 mM alkali concentration, the purity of the p(3HB-co-3HH) powder was 72% and 70% respectively, and the average molecular weights of the polymers were 870,000 and 650,000, respectively. It was, therefore, clear that the purity of the p(3HB-co-3HH) powder obtainable by this method is low and that the decrease in polymer molecular weight is remarkable in the case of 8 mM.

INDUSTRIAL APPLICABILITY

The method of the present invention for separating and purifying PHA can provide PHA of high purity according to a very simple separation and purification protocol. By the method of the invention, the pH of the suspension can be controlled with high precision and PHA of high purity can be obtained with good efficiency without incurring a serious decrease in molecular weight of the product PHA. Therefore, the invention contributes a great deal to improved efficiency and cost reduction of the commercial production of PHA by means of microorganisms.

The invention claimed is:

1. A method of producing a poly-3-hydroxyalkanoic acid, which comprises carrying out a physical disruption treatment of a suspension of poly-3-hydroxyalkanoic acid-containing microbial cells with adding an alkali thereto either continuously or intermittently and, thereafter, separating the poly-3-hydroxyalkanoic acid.

2. The method according to claim 1,
wherein said addition of an alkali is carried out with controlling the pH of the suspension.

3. The method according to claim 2,
wherein the pH of the suspension is controlled between 9 and 13.5.

4. The method according to claim 1,
wherein said physical disruption treatment is carried out under stirring of said suspension.

5. The method according to claim 1,
wherein said physical disruption treatment is carried out at the temperature not less than 20° C. and below 40° C.

6. The method according to claim 1,
wherein the poly-3-hydroxyalkanoic acid is a copolymer comprising of D-3-hydroxyhexanoate (3HH) and one or more other 3-hydroxyalkanoic acids.

7. The method according to claim 6,
wherein the poly-3-hydroxyalkanoic acid is a binary copolymer comprising of D-3-hydroxybutyrate (3HB) and D-3-hydroxyhexanoate (3HH) or a ternary copolymer comprising of D-3-hydroxybutyrate (3HB), D-3-hydroxyvalerate (3HV), and D-3-hydroxyhexanoate (3HH).

8. The method according to claim 1,
wherein the poly-3-hydroxyalkanoic acid-containing microbial cells are cells of *Aeromonas caviae*.

9. The method according to claim 1,
wherein the poly-3-hydroxyalkanoic acid-containing microbial cells are cells of a strain of microorganism transformed by a poly-3-hydroxyalkanoic acid synthase group gene derived from *Aeromonas caviae*.

* * * * *